United States Patent [19]
Arnold

[11] Patent Number: 5,827,945
[45] Date of Patent: Oct. 27, 1998

[54] REAL-TIME GAS-CHROMATOGRAPHY MASS-SPECTROMETRY TRACE VAPOR DETECTION

[75] Inventor: James T. Arnold, Sunnyvale, Calif.

[73] Assignee: Varian Associates, Inc., Palo Alto, Calif.

[21] Appl. No.: 738,961

[22] Filed: Oct. 24, 1996

[51] Int. Cl.⁶ .................................................. G01N 30/08
[52] U.S. Cl. ........................................... 73/23.42; 96/105
[58] Field of Search .............................. 73/23.35, 23.41, 73/23.42; 96/105

[56] References Cited

U.S. PATENT DOCUMENTS

| | | | |
|---|---|---|---|
| 3,427,863 | 2/1969 | Schultz | 73/23.35 X |
| 5,014,541 | 5/1991 | Sides et al. | 73/23.41 |
| 5,152,176 | 10/1992 | Bryselbout et al. | 73/23.35 X |
| 5,268,302 | 12/1993 | Rounbehler et al. | 73/23.41 X |

*Primary Examiner*—Michael Brock
*Attorney, Agent, or Firm*—Edward Berkowitz

[57] ABSTRACT

A gas flow distribution system accumulates a sample from a sample bearing carrier gas in a micro-accumulator, delivers it using a carrier gas to a gas chromatography column, and supplies a carrier gas to the gas chromatography column to facilitate separation of the sample into sample components and transport the sample components to a mass spectrometer for trace vapor detection and analysis or testing in real time. The system is made of inert components and configured to have low dead volume for improved performance and accuracy of detection. External valves are employed for easy management and balance of the flow in the system to minimize operation time and facilitate continuous accumulation, delivery, and testing of the sample. The delivery of the sample to the gas chromatography column using an electrically heated cold trap as the micro-accumulator can be performed extremely fast. By further combining the sample accumulation phase and the sample testing phase, real time operation of trace vapor detection is achieved. Because the step of delivering the sample to the gas chromatography column is performed quickly, the accumulation of the sample can resume quickly and is nearly continuous for improved efficiency.

21 Claims, 3 Drawing Sheets

REAL-TIME GAS-CHROMATOGRAPHY MASS-SPECTROMETRY TRACE VAPOR DETECTION

FIELD OF THE INVENTION

This invention relates generally to trace vapor detection using gas chromatography and mass spectrometry, and more particular to the real-time accumulation and delivery of a trace vapor sample to a gas chromatography column and mass spectrometer for trace vapor detection and analysis.

BACKGROUND OF THE INVENTION

A gas-chromatography mass-spectrometry (GC/MS) technique may be used for analyzing gas mixtures. In such an application, the gas chromatography (GC) column separates sample components from the sample gas mixture and the separated components are chemically analyzed in the mass spectrometer.

The application of the GC/MS technique to trace vapor detection and analysis imposes stringent requirements on the acquisition and introduction of the sample to the trace vapor detector. Gas chromatography requires the introduction of a sample in a concentrated pulse. The distribution of trace vapor in the sampling environment of ambient air, however, is extremely diffuse. Although fast gas chromatography employing a capillary column is available for separating sample components on the order of about ten seconds, limitations in commercially available equipment, especially the sample inlet system, have prevented general application of high-speed gas chromatography. In particular, traditional methods of accumulating a trace vapor sample with the proper pulse concentration for delivery to the GC column are too slow for realistic application in trace vapor detection.

One method to improve the inlet system is the use of a vapor collection cold trap as the inlet device. After accumulation of the trace vapor sample in the cold trap, the inlet device is heated to input quickly the collected sample to the GC column. See, e.g., R. F. Mouradian et al., *Evaluation of a Nitrogen-Cooled, Electrically Heated Cold Trap Inlet for High-Speed Gas Chromatography*, 28 J. CHROMATOGRAPHIC SCIENCE 643–48 (December 1990).

To achieve a practical GC/MS trace vapor detection system, the accumulation and delivery of the trace vapor sample to the GC column and the separation and analysis of the sample must occur in real time, i.e., in a matter of minutes or preferably seconds. However, even with the development of the cold trap inlet system, the GC/MS methodology has not been adapted for general application in trace vapor analysis and detection. Furthermore, existing methods of directing the sample flow through a collection device such as the cold trap and through the GC column to the mass spectrometer do not make full use of the speed of the individual instrument components to facilitate flow distribution and achieve real time trace vapor detection.

SUMMARY OF THE INVENTION

An object of this invention is to provide a real time GC/MS trace vapor detection and analysis system that captures and accumulates a trace vapor sample, retains the sample against a demand for delivery to the GC column for separation, separates the sample through the GC column into sample components, and analyzes the sample components in the mass spectrometer, all in real time, i.e., under about 30 seconds.

It is a further object of this invention to minimize dead volume and eliminate contaminants in the trace vapor detection and analysis system to ensure integrity of the system and accuracy of detection and analysis.

It is yet another object of the present invention to employ pure carrier gas to direct the sample flow to achieve superior flow control in the trace vapor detection system and eliminate electrical and mechanical problems associated with traditional electro-mechanical flow control devices.

In accordance with one aspect of this invention, a gas flow distribution system for controlled accumulation and delivery of a sample in a diffused state for trace vapor detection and analysis comprises a sample delivery circuit, a sample bearing carrier gas influent circuit, a GC carrier gas influent circuit, and a distribution carrier gas influent circuit. The sample delivery circuit includes a sample accumulator for accumulating the sample in an accumulation cycle. At the time for sample delivery to a gas chromatography column, the accumulator is in communication with a gas chromatography column for receiving the sample in a delivery cycle for separating the sample in a separation cycle. The sample bearing carrier gas influent circuit includes a supply of sample bearing carrier gas to the sample delivery circuit through the sample accumulator for accumulation of the sample in the sample accumulator in real time. The sample bearing carrier gas influent circuit further includes a sample diversion switch for diverting the sample bearing carrier gas from the sample delivery circuit in the delivery cycle. The GC carrier gas influent circuit includes a supply of GC carrier gas through the sample delivery circuit to the gas chromatography column for sample separation in real time. A GC carrier gas diversion switch diverts the GC carrier gas from the sample delivery circuit in the delivery cycle. The distribution carrier gas influent circuit includes a supply of distribution carrier gas to deliver the sample in the accumulator to the gas chromatography column in the delivery cycle in a short pulse on demand. A drain switch diverts the distribution carrier gas from the sample delivery circuit in the accumulation cycle and separation cycle.

Another aspect of the present invention is a gas control circuit for supplying a sample to a gas chromatography column in a trace vapor detection system. The gas control circuit comprises a supply of sample bearing carrier gas which includes a sample. The gas control circuit further comprises a supply of carrier gas, a sample accumulating means, and a means for directing the sample bearing carrier gas to the sample accumulating means for accumulation of the sample in the sample accumulating means in real time and for diverting the distribution carrier gas from entering the sample accumulating means in an accumulation mode. The gas control circuit also comprises a means for transferring the sample accumulated in the sample accumulating means to the gas chromatography column for separation in real time with the carrier gas and diverting the sample bearing carrier gas from entering the sample accumulating means in a delivery mode.

Yet another aspect of this invention is a gas flow circuit for real-time accumulation and delivery of a sample to a gas chromatography column. The gas flow circuit comprises a manifold, a sample influent line for introducing a sample bearing carrier gas into the manifold, a detection carrier gas influent line for introducing a detection carrier gas into the manifold, a distribution carrier gas influent line for introducing a distribution carrier gas into the manifold, and an accumulator. The sample influent line includes a sample diversion line with a sample diversion valve. The detection carrier gas influent line is in communication with the gas chromatography column through the manifold and includes a detection carrier gas diversion line with a detection carrier gas diversion valve. The distribution carrier gas influent line includes a distribution carrier gas diversion line with a distribution carrier gas diversion valve. The accumulator is disposed between the distribution carrier gas influent line and the manifold. The accumulator is downstream of the sample influent line and manifold and upstream of the distribution carrier gas diversion line, and the gas chromatography column is downstream of the detection carrier gas influent line and manifold, when the distribution carrier gas diversion valve is opened, and the sample diversion valve and detection carrier gas diversion valve are closed. The accumulator is downstream of the distribution carrier gas influent line and upstream of the manifold and gas chromatography column when the distribution carrier gas diversion valve is closed and the sample diversion valve and detection carrier gas diversion valve are opened.

In accordance with another aspect of the present invention, a method of detecting and analyzing trace vapor using gas chromatography and mass spectrometer comprises the following steps. A sample bearing carrier gas is provided through an accumulator which captures and accumulates a sample from the sample bearing carrier gas in real time. The sample bearing carrier gas is diverted from the accumulator upon accumulation of the sample in the accumulator, and a carrier gas is directed through the accumulator to transfer the sample to the gas chromatography column in real time. A GC carrier gas is supplied through the gas chromatography column to separate the sample into sample components and transport the sample components to the mass spectrometer in real time.

BRIEF DESCRIPTION OF THE DRAWINGS

The preferred embodiments of this invention, illustrating all their features, will now be discussed in detail. These embodiments depict the novel and nonobvious system and method for GC/MS trace vapor detection of this invention shown in the accompanying drawings, which are included for illustrative purposes only. These drawings include the following figures, with like numerals indicating like parts.

DETAILED DESCRIPTION OF THE INVENTION

Figure 1:
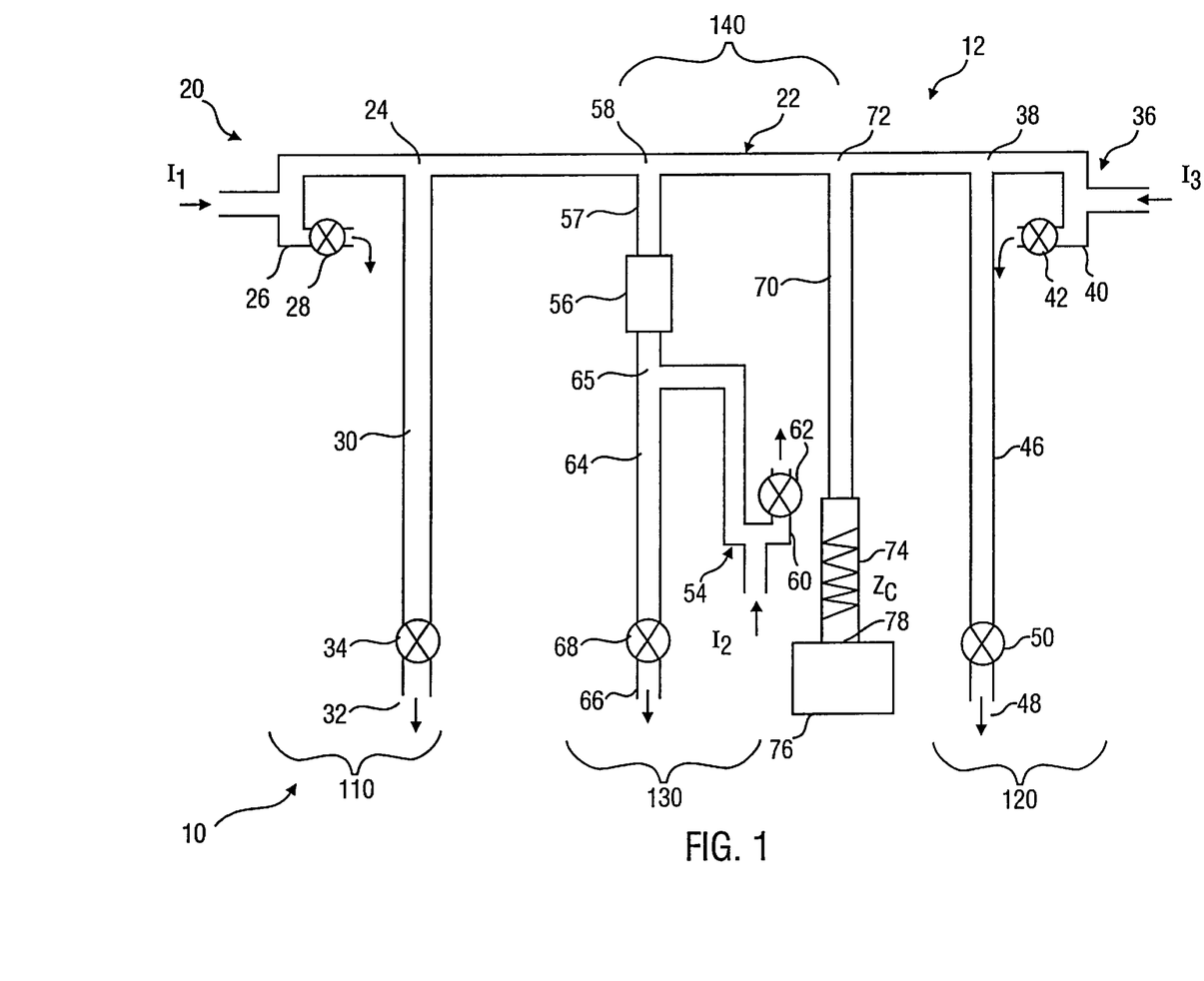
FIG. 1 is a schematic view of the gas-chromatography mass-spectrometry trace vapor detection system illustrating the exemplary embodiment of the gas flow distribution circuit of the present invention.

Referring to FIG. 1, a schematically illustrated trace vapor detection and analysis system 10 employs a gas flow distribution system or control circuit 12 to direct a trace vapor sample through the detection and analysis system 10. The flow control system 12 advantageously employs the use of clean carrier gas to control delivery of the sample, thereby eliminating problems associated with traditional electromechanical devices.

A. Gas Flow Distribution System

In the exemplary embodiment of the gas flow distribution circuit 12 shown in FIG. 1, there are three gas flow inlets. The first inlet, a sample bearing carrier gas inlet 20, is connected to a gas distribution manifold 22 at a sample bearing carrier gas influent juncture 24. The first inlet 20 desirably includes a sample flow adjustment line 26 and valve or switch 28. A sample bearing carrier gas diversion line 30 extends to the influent juncture 24 between the first inlet 20 and the manifold 22. The diversion line 30 has a diversion exit or outlet 32, and desirably includes a sample bearing carrier gas diversion valve or switch 34 near the diversion outlet 32.

A second inlet, a detection or GC carrier gas inlet 36, is connected to the gas distribution manifold 22 at a GC carrier gas influent juncture 38, and preferably has a GC carrier gas flow adjustment line 40 and valve or switch 42. Connected between the GC carrier gas inlet 36 and the manifold 22 at the influent juncture 38 is a GC carrier gas diversion line 46 with a diversion exit or outlet 48. A GC carrier gas diversion switch or valve 50 is desirably disposed near the diversion exit 48.

A third inlet, a distribution or delivery carrier gas inlet 54, is connected to one side of a sample accumulator 56. The other side of the sample accumulator 56 is connected to the manifold 22 through an accumulator flow line 57 at an accumulator flow influent juncture 58, which is advantageously placed between the sample bearing carrier gas influent juncture 24 and the GC carrier gas influent juncture 38. The third inlet 54 desirably includes a distribution or delivery carrier gas adjustment line 60 with an adjustment switch or valve 62. A distribution carrier gas diversion line or drain line 64 is connected between the accumulator 56 and the third inlet 54 at a distribution or delivery carrier gas influent juncture 65. The drain line 64 has a drain or diversion outlet 66 with a drain or diversion valve 68. In some cases, there may be provided vacuum sinks (not shown) at the diversion outlets 32, 48, and 66.

A GC influent line 70 connects with the gas distribution manifold 22 at a GC influent juncture 72, which is preferably disposed between the accumulator flow influent juncture 58 and the GC carrier gas influent juncture 38. The GC influent line 70 supplies a GC column 74 and a mass spectrometer 76 adjacent the output end or exit 78 of the GC column. The inlet flow rate $I_1$ into the sample bearing carrier gas inlet 20, the inlet flow rate $I_2$ into the distribution carrier gas inlet 54, and the inlet flow rate $I_3$ into the GC carrier gas inlet 36 desirably are individually constant. Providing constant flow rates is advantageous for GC analysis because they produce consistent GC operation. These flow rates if adjusted to different constant rates will still be advantageous for GC separation as long as they are repeatable.

To achieve such flow rates, the manifold 22, diversion lines 30, 46, 64, GC influent line 70, and accumulator flow line 57 are preferably longitudinal tubes of a generally circular shape with individually constant diameters. For a GC column 74 of about 180 micron inner diameter, the diameters of the manifold 22, diversion lines 30, 46, 64, GC influent line 70, and accumulator flow line 57 may be in the neighborhood of 180 micron but may generally be as large as above 500 micron. A 180 micron diameter for the internal flow lines such as the manifold 22, GC influent line 70, and accumulator flow line 57 may be desirable to shorten time for the gas flows to reach their destination and decrease the overall operation time, since the internal volume will be decreased. The preferred diameters are about 500 micron for the manifold 22, about 180 micron for the GC influent line 70, and about 500 micron for the accumulator flow line 57. The diversion line 30 desirably is about 500 micron in diameter, the diversion line 46 about 500 micron in diameter, and the diversion line 64 about 500 micron in diameter.

In the exemplary embodiment, the distance of the flow path between the sample accumulator 56 and the GC column 74 through junctures 58, 72 is preferably less than about 5 cm. This ensures prompt delivery of the sample from the accumulator 56 to the GC column 74 as discussed below. The lengths of the other components and their corresponding internal volumes are not critical to the general operation of the detection system 10, but should be coordinated for real time operation. The preferred length of the manifold 22 from the influent juncture 24 to the influent juncture 38 is less than 12 cm. The lengths of the diversion lines 30, 46, and 64 are preferably less than 20 cm, and are more preferably 15 cm.

The structure and function of the sample accumulator 56 are described below. Suitable GC column 74 and mass spectrometer 76 are known in the art and the details thereof will not be described here. A preferred embodiment of the GC column 74 has an internal volume of about 1/10 c.c. and an inner diameter of about 180 micron, which can achieve fast GC separation of some desired samples in about 10–15 seconds. This type of GC column 74 is suitable for real time trace vapor detection and analysis in the detection system 10. Note that the preferred internal volume of the GC column 74 will depend in part on the samples selected for separation.

The components are desirably arranged to achieve low dead volume in the detection system 10, which is determined in part by the configuration and sizes of the components. As a general rule, the GC resolution is inversely proportional to the dead volume percentage. For instance, a GC resolution of 10 may be realized in a 1/10 c.c. GC column if the dead volume is about 1/100 c.c. Accordingly, the dead volume allowed in the system 10 is approximately equal to or less than the reciprocal of the required GC resolution multiplied by the internal volume of the GC column.

In operation, at least the internal operating parts of the detection system 10, including the manifold 22, sample accumulator 56, and GC influent line 70 are placed in a high-temperature oven, for example, at a temperature of greater than about 200° C. for certain samples. The high-temperature environment ensures proper flow within the flow distribution circuit 12 and prevents cold spots from forming and clogging in the circuit 12, which may otherwise lead to poor analysis results with undesirable spreading of the gas peaks in the gas chromatography column and mass spectrometry analysis.

To maintain the integrity of the trace vapor detection and analysis system 10 and the accuracy of analysis, the components of the system 10 preferably have nonreactive interiors with which the various gases make contact. The components may be made entirely of nonreactive or inert material, such as glass or quartz. Quartz components are fragile, and may be difficult to handle. Commercially available quartz-lined stainless steel components are preferred because the stainless steel lined with silica is less fragile and more flexible and durable. Other suitable inert material not mentioned can also be used.

The valves 28, 34, 42, 50, 62, 68 are used to manage the flow distribution in the circuit 12 and preferably have low volumes to minimize the time delay in switching the valves on and off. These valves are advantageously located exterior of the internal operating parts of the detection system 10 and the oven for easy operation outside of the high-temperature zone and thus need not be qualified for high temperature. The valves are also advantageously located downstream of the internal flow paths of the system 10 so that those flows do not enter the sample measurement streams. Note that, as discussed below, the diversion valve 50 may be eliminated, provided that the line 46 has a suitable impedance to the drain, because the adjustment valve 42 is adequate in controlling the flow of the GC carrier gas 13 as long as the flow can be controlled to provide adequate pressure at the influent juncture 38 to avoid backflow when necessary. This configuration minimizes the introduction of dead volume by the valves 28, 34, 42, 50, 62, 68 into the system 10, as described in more detail below. A commercially available valve that is sufficiently inert and suitable for controlling the flow in the distribution circuit 12 is an electrically operated valve furnished by Clippard Instrument Laboratory, Inc.

The various components of the detection system 10 may be assembled using any suitable method. For instance, if the components are made of quartz, fusible "solder glass" may be used to seal the joints. Alternatively, silica lined stainless steel, commercially known as Silco Steel, may be used for tubing and connection fittings between the components. In a different embodiment, the entire detection system 10 may be a monolithic system made by microlithography, a method widely used for integrated circuit manufacturing.

1. Sample Bearing Carrier Gas Generator

The supply of sample bearing carrier gas into the inlet 20 can be generated in a variety of ways. An example of a sample bearing carrier gas generator 90 is the membrane separator shown in FIG. 2. The membrane separator 90 comprises a chamber 92 with an air inlet 94a for receiving ambient air into a space 94c, an exit port or vent 94b for the sample depleted air, an exit port or vent 101 for any residual sample depleted air, a carrier gas inlet 95 for receiving carrier gas into a space 102, and an outlet 96 for output of sample bearing carrier gas. Inside the chamber 92 are two membranes 98, 99 spaced from each other and disposed in the path of flow from the space 94c to the space 102. Each membrane 98, 99 may be made of a silicone rubber film backed by a porous substrate support plate and sealed across the cross-section of the chamber 92. The membranes 98, 99 define a space 100 therebetween and separate the spaces 94c and 102. The sample constituents in the input air, such as hydrocarbons, are dissolved in the silicone rubber and diffuse through the membranes 98, 99 to the other side, moving downstream of their partial pressure gradient.

Figure 2:
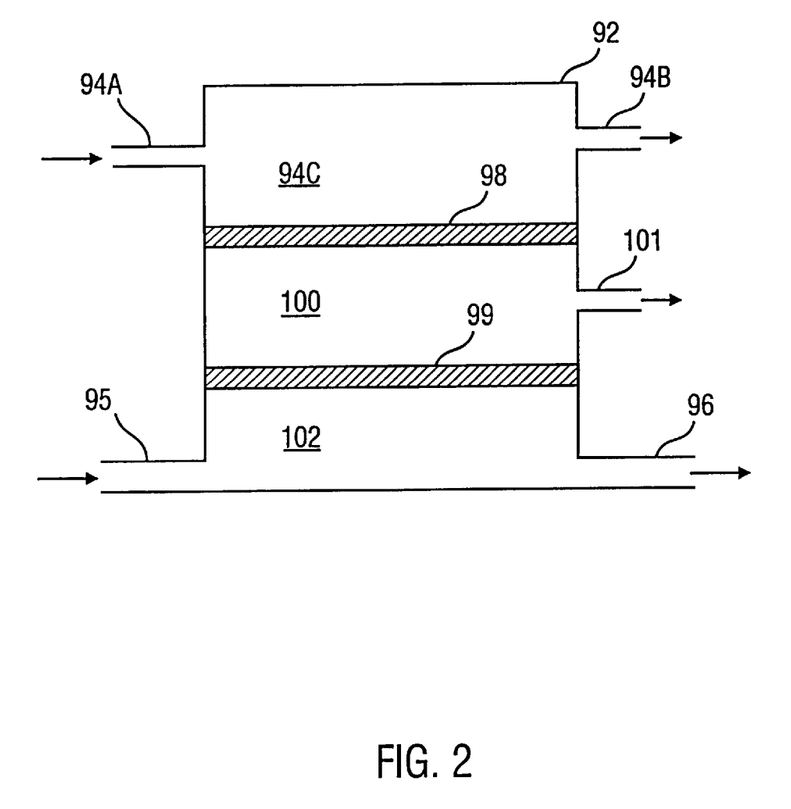
FIG. 2 is a schematic view of the sample bearing carrier gas generator for supplying the sample bearing carrier gas to the gas flow distribution circuit.

The first membrane 98 is disposed near the inlet 94 and allows passage of the gas constituents of the sample in the input air therethrough. The first membrane 98 blocks off much of the air. The small amount of air transpiring the membrane 98 is mostly vented out of the space 94c to a vacuum pump (not shown) via the exit port 94b. The sample passes through the second membrane 99 to the other side of the chamber 92 adjacent the carrier gas inlet 95 and outlet 96. The clean carrier gas mixes with the sample and carries it through the outlet 96 in the form of a sample bearing carrier gas which may be fed into the sample bearing carrier gas inlet 20 of FIG. 1. This outflow maintains the sample partial gradient that drives the sample flow through the separator 90. It is understood that other suitable sample bearing carrier gas generating methods can be used as well.

2. Sample Bearing Carrier Gas Influent Circuit

Referring to FIG. 1, a sample bearing carrier gas influent circuit 110 comprises the sample bearing carrier gas inlet 20, diversion line 30, and diversion valve 34. The influent circuit 110 controls the supply of the sample bearing carrier gas through the manifold 22 into the sample accumulator 56 for capture and accumulation of the sample. The sample flow adjustment valve 28 is used to adjust the flow rate $I_1$ of the sample bearing carrier gas, which may be constant, into the manifold 22 by adjusting the amount of flow through the sample flow adjustment line 26. The faster the flow through the sample flow adjustment line 26, the slower the flow rate $I_1$ at which the sample bearing carrier gas enters the manifold 22. The diversion valve 34 may be closed to direct the flow of the sample bearing carrier gas to the sample accumulator 56 or opened to divert the flow away from the accumulator 56 at the influent juncture 24 and through the diversion line 30 out the diversion exit 32. The flow path of the sample bearing carrier gas advantageously does not cross either of the valves 28, 34, and thus avoids the buildup of dead volume or contamination in the system 10 contributed by the valves 28, 34.

Backflow from the manifold 22 to the influent circuit 110 during diversion of the flow may pose a problem. When the diversion valve 34 is opened to divert flow through the diversion line 30, the sample flow adjustment valve 28 is desirably adjusted to maintain proper pressure in the vicinity of the influent juncture 24 to prevent backflow from the manifold 22 to the sample bearing carrier gas influent circuit 110. In an alternative embodiment, the diversion valve 34 may also be made adjustable to control the pressure in the influent circuit 110. In that case, the adjustment of either the sample flow adjustment valve 28 or the diversion valve 34 is generally sufficient to achieve a pressure to prevent backflow into the influent circuit 110.

3. GC Carrier Gas Influent Circuit

As illustrated in FIG. 1, a GC carrier gas influent circuit 120 comprises the GC carrier gas inlet 36, diversion line 46, and diversion valve 50. The influent circuit 120 controls the supply of the GC carrier gas through the manifold 22 and GC influent line 70 into the GC column 74 to push the sample through the GC column for separation and the mass spectrometer 76 for analysis. The flow adjustment valve 42 is used to adjust the flow rate $I_3$ of the GC carrier gas, which may be a constant rate, into the manifold 22 by adjusting the amount of flow through the flow adjustment line 40. The diversion valve 50 may be closed to direct the flow of the GC carrier gas to the GC influent line 70 or opened to divert the flow away from the GC influent line 70 at the influent juncture 38 and through the diversion line 46 out the diversion exit 48. The flow path of the GC carrier gas into the manifold 22 advantageously does not cross either of the valves 42, 50, and thus avoids the buildup of dead volume or contamination in the system 10 contributed by them.

To prevent backflow from the manifold 22 to the GC carrier gas influent circuit 120 when the diversion valve 50 is opened to divert flow through the diversion line 46, the flow adjustment valve 42 may be adjusted to maintain proper pressure in the vicinity of the influent juncture. In an alternative embodiment, the diversion valve 50 may also be adjustable to control the pressure in the influent circuit 120. The adjustment of either the flow adjustment valve 42 or the diversion valve 50 alone may be sufficient to achieve a pressure to prevent backflow into the influent circuit 120 in that event. It is noted that, with appropriate impedance in diversion line 46 defined by its bore size, the diversion valve 50 may be eliminated because the adjustment valve 42 is sufficient to control the flow of the GC carrier gas into the manifold 22 as long as sufficient flow rate $I_3$ can be generated to support adequate pressure at the influent juncture 38 to prevent backflow when necessary.

4. Distribution Carrier Gas Influent Circuit

FIG. 1 shows a distribution or delivery carrier gas influent circuit 130 that comprises the distribution or delivery carrier gas inlet 54, diversion or drain line 64, and diversion or drain valve 68. The influent circuit 130 controls the supply of the distribution carrier gas through the sample accumulator 56 to drive the sample collected therein through the manifold 22 and the GC influent line 70 to the GC column 74. The flow adjustment valve 62 is used to adjust the flow rate $I_2$ of the distribution carrier gas, which may be constant, into the accumulator 56 by adjusting the amount of flow through the flow adjustment line 60. The drain valve 68 may be closed to direct the flow of the distribution carrier gas to the accumulator 56 or opened to divert the flow away from the accumulator 56 at the influent juncture 65 and through the drain line 64 out the drain exit 66. The flow path of the distribution carrier gas into the manifold 22 advantageously does not cross either of the valves 62, 68, and avoids the buildup of dead volume or contamination in the system 10 which might otherwise be contributed by the valves 62, 68.

When the drain valve 68 is opened to divert flow through the drain line 64, the flow adjustment valve 62 may be adjusted to maintain proper pressure in the vicinity of the distribution carrier gas influent juncture 65 to prevent an interfering flow from the distribution carrier gas influent circuit 130 to the accumulator 56 or into the GC influent line 70. Instead, the flow of the distribution carrier gas facilitates the flow of the sample bearing carrier gas from the inlet circuit 110 through the accumulator 56 out the drain exit 66. In an alternative embodiment, the drain valve 68 may also be adjustable to control the pressure in the influent circuit 130. Indeed, the adjustment of either the flow adjustment valve 62 or the diversion valve 68 alone may be sufficient to achieve a pressure to prevent backflow into the influent circuit 130.

5. Sample Delivery Circuit

A sample delivery circuit 140 comprises the manifold 22, sample accumulator 56, and GC influent line 70, which leads to the GC column 74 and mass spectrometer 76, as shown in FIG. 1. The sample accumulator 56 captures and collects sample from the flow of sample bearing carrier gas that enters the manifold 22 from the first inlet 20 and passes through the accumulator flow line 57 to the accumulator 56. Upon accumulating a sufficient amount of sample, the sample in the accumulator 56 is released by a thermal pulse and supplies the sample through the manifold 22 and GC influent line 70 to the GC column 74. In that transfer of the sample, the direction of flow through the accumulator 56 is reversed. The distribution carrier gas enters the third inlet 54 and passes through the sample accumulator 56 to carry the sample through the accumulator flow line 57 and manifold 22 to the GC influent line 70. At that point, the sample is ready for separation in sample components in the GC column 74, and the distribution carrier gas is diverted from the sample accumulator 56. To facilitate the separation of the sample in the GC column 74, the GC carrier gas enters from the second inlet 36 through the manifold 22 and GC influent line 70 to push the sample through the GC column 74.

For a balance of flow in the flow distribution circuit 12, there is preferably sufficient pressure at the GC influent juncture 72 to prevent the sample bearing carrier gas from flowing directly into the GC column 74 when it enters the sample accumulator 56 for sample collection through the manifold 22. This pressure may be maintained by an impedance $Z_c$ in the GC column 74 created by the bore size of the GC column 74 which restricts the flow through the GC influent line 70. In a preferred embodiment, the GC carrier gas from the second inlet 36 flows through the GC influent line 70 for sample separation simultaneously with the flow of sample bearing carrier gas from the first inlet 20 through the accumulator 56 for accumulation. In that case, the pressure of the GC carrier gas maintains pressure at the GC influent juncture 72 to prevent direct flow of the sample bearing carrier gas into the GC influent line 70. Likewise, the flow of the sample bearing carrier gas to the accumulator 56 supports a pressure at the accumulator flow influent juncture 58 to prevent direct flow of the GC carrier gas through the manifold 22 and accumulator flow line 57 into the accumulator 56. As a result, the sample bearing carrier gas and the GC carrier gas are isolated from each other.

Furthermore, during the flow of the distribution carrier gas from the third inlet 54 through the accumulator 56 and manifold 22 to the GC influent line 70, there is preferably sufficient pressure buildup at the accumulator flow influent juncture 58 and GC influent juncture 72 to prevent an interfering flow from either the sample bearing carrier gas influent circuit 110 or GC carrier gas influent circuit 120. This balance of flow is accomplished by manipulating the valves 28, 34, 42, 50, 62, 68 in a precision-timed fashion as well as by appropriate values of the inherent impedances in the flow lines determined by their bore sizes. A computer or similar device (not shown) may be incorporated to manage the valves automatically.

The sample accumulator 56 is advantageously chosen to capture and accumulate sufficient amount of sample from the sample bearing carrier gas in real time, preferably within 10–20 seconds, and to transfer the collected sample to the GC column 74 assisted by the flow of the distribution carrier gas also in a matter of seconds, preferably 1–2 seconds. The exemplary embodiment of the sample accumulator 56 uses an electrically heated cold trap (not shown) similar to the one described in the Mouradian article. The sample is captured and collected inside the accumulator 56, cooled by, for example, cold nitrogen gas. The sample accumulation volume of the accumulator 56 is preferably about 5 microliter for the exemplary embodiment. Because of this small volume, the sample accumulator 56 used in the detection system 10 can be characterized as a micro-accumulator. Upon accumulation of the proper amount of sample, a time period that is typically 10–20 seconds, but that can be varied to suit the enrichment level of the sample in the sample bearing carrier gas and the cold trap capturing parameters, the accumulator 56 is automatically electrically heated by, for instance, a large pulse of current through wiring connected to the accumulator 56. This large pulse of current generates a ballistic temperature rise in the accumulator 56 that causes a nearly instantaneous heating for rapid reflux of the sample from the accumulator 56 to the GC column 74 along the flow produced by the distribution carrier gas of the third inlet 54.

B. Operation of the Gas Flow Distribution System

The operation of the gas flow distribution system 12 of FIG. 1 is thus divided into three phases. In the accumulation phase, the sample accumulator 56 accumulates the sample from the sample bearing carrier gas. In the accumulated sample delivery or reflux phase, the distribution carrier gas transfers the collected sample in the accumulator 56 to the GC column 74. In the detection or separation phase, the GC carrier gas drives the sample through the GC column 74 for separation and the mass spectrometer 76 for analysis. The third phase of a cycle is usually concurrent with the first phase of the successive cycle.

1. Accumulation Phase

The sample bearing carrier gas supplies the sample to the sample accumulator 56 to charge the accumulator 56 during the accumulation phase. The flow path of the sample bearing carrier gas begins at the inlet 20 through the influent juncture 24 to the manifold 22. The sample flow adjustment valve 28 is set to regulate the gas flow rate $I_1$. The flow continues past the accumulator flow influent juncture 58 to the accumulator flow line 57. The sample bearing carrier gas continues through the accumulator 56 in which the sample is captured, and passes through the drain line 64 and the opened drain valve 68 out the drain exit 66. During this phase, the sample bearing carrier gas diversion valve 34 is closed so that the gas is not diverted from entry into the sample accumulator 56. There is sufficient pressure buildup at the GC influent juncture 72 to prevent the sample bearing carrier gas from flowing through the manifold 22 and into the GC influent line 70. This pressure buildup can be accomplished by manipulating the GC carrier gas diversion valve 50 and the adjustment valve 42 to control the GC carrier gas flow, such as by closing both valves 50, 42. To realize real time operation, the sample accumulator 56 is preferably chosen to accumulate the proper amount of sample in about 10–20 seconds.

2. Accumulated Sample Delivery Phase

In the delivery or reflux phase, the sample bearing carrier gas is diverted through the diversion line 30 out through the opened diversion valve 34. The drain valve 68 is closed to allow the distribution carrier gas to flow from the third inlet 54 through the juncture 65 to the sample accumulator 56. The distribution carrier gas passes through the sample accumulator 56 in a reverse flow to establish a flow path through the accumulator flow line 57, the manifold 22, and the GC influent line 70 to the GC column 74. The GC carrier gas diversion valve 50 is opened to divert the flow of the GC carrier gas from the second inlet 36 through the diversion line 46 out the diversion exit 48. The manipulation of the diversion valves 34, 68, 50 balances the different flows in the system 12 and achieve this flow pattern by ensuring sufficient pressure at the sample bearing carrier gas influent juncture 24 and the GC carrier gas influent juncture 38 to eliminate backflows as discussed above.

To supply the accumulated sample in the cold trap of the accumulator 56 to the GC column 74, a large pulse of current is applied to the heater in the accumulator 56 to provide a ballistic temperature rise in the accumulator 56. This almost instantaneous heating provides for very rapid reflux of the sample from the sample accumulator 56 to discharge the accumulator and deliver the sample to the GC influent line 70 to start the separation process. As mentioned above, to facilitate the reflux in the exemplary embodiment, the distance between the accumulator 56 and the GC column 74 is less than about 5 cm. The time involved in the delivery phase of the operation is preferably from 1–2 seconds, and more preferably about 1 second.

3. Detection Phase

The flow that governs the detection phase is that of the GC carrier gas, which pushes the sample that has been delivered to the GC influent line 70 through the GC column 74 for separation of the sample into sample components for analysis in the mass spectrometer 76. The GC carrier gas flow path begins at the second inlet 36 through the influent junctures 38, 72 at the manifold 22 to the GC influent line 70, and then through the GC column 74 out the exit 78 to deliver the separated components to the mass spectrometer 76. To establish such a flow, the GC carrier gas diversion valve 50 is closed to eliminate diversion of the gas flow to the manifold 22. There is preferably sufficient pressure in the manifold 22 at the accumulator flow influent juncture 58 to prevent the GC carrier gas from flowing into the sample accumulator 56. This can be achieved by manipulating the diversion valves 34, 68, for instance, by closing the diversion valve 34 and opening the drain valve 68. This action also starts the next cycle's accumulation phase.

For real-time operation, the GC column 74 preferably performs the separation of the sample in about 10–20 seconds. The duration of the detection phase therefore should have about the same range, preferably within the range of about 10 to 20 seconds.

4. Continuous Flow Circuit

In the exemplary embodiment of the flow distribution circuit 12, the efficient arrangement of the flow paths are utilized to reduce operation time and minimize dead volume in the circuit 12. One efficient manner of controlling the flow distribution is by operating the circuit 12 in the accumulation phase and the detection phase, as noted, simultaneously. In this combined accumulation-detection phase, the diversion valves 34, 50 are closed and the drain valve 68 is opened. The sample bearing carrier gas ($I_1$) flows through the sample accumulator 56 for accumulation of the sample in the accumulator 56 and out through the drain valve 68. At the same time, the GC carrier gas ($I_3$) flows through the GC column 74 to push the sample delivered to the GC influent line 70 in a previous delivery phase through the GC column 74 for separation and the mass spectrometer 76 for analysis. The two flows $I_1$ and $I_3$ occur simultaneously and support proper pressure in the manifold 22 between the influent junctures 58 and 72 to isolate the GC carrier gas flow from the sample bearing carrier gas flow to prevent flow interference with each other. The accumulation phase and detection phase are advantageously coordinated to be completed within the same period of time.

At the completion of the combined accumulation-detection phase, the accumulated sample delivery phase takes place by opening the diversion valves 34, 50 to divert the sample bearing carrier gas flow and GC carrier gas flow from the sample delivery circuit 140. The drain valve 68 is closed to allow the distribution carrier gas to direct the sample from the accumulator 56 to the GC influent line 70, to be positioned for separation by the GC column during the detection phase in the next cycle. The current operation cycle is completed with the delivery of the sample and the diversion valves 34, 50, 68 are reset to start the accumulation-detection phase of the next operation cycle. The flow through the distribution circuit 12 is facilitated by the high-temperature environment of the oven (not shown) keeping the internal flow of the circuit 12, for example, above 200° C. and avoiding cold spots. The entire operation cycle preferably lasts about 10–20 seconds, and more preferably is completed in about 15 seconds.

This flow sequence establishes a continuous flow in the flow distribution circuit 12 and reduces the time required for an operation cycle. The continuous flow in the circuit 12 avoids the introduction of dead volume and makes efficient use of the arrangement of the flow paths. The arrangement further achieves nearly a continuous accumulation of the sample in the sample accumulator 56 and diverts very little sample through the drain line 64 during the short delivery phase. The operation cycle is easily managed by controlling the three diversion valves, 34, 50, 68. Preferably, the diversion valves 34, 50, 68 and the flow modulating adjustment valves 28, 42, 62 are disposed exterior of the sample delivery circuit 140. In short, the gas distribution system 12 is efficient, uncontaminated, easy to operate, and accomplishes in real time the capture, separation, and detection of the trace vapor sample.

Furthermore, the entire detection system 10 is generally small and can be made transportable for use in the field for collecting and detecting trace vapor samples. This real time GC/MS trace vapor detection scheme is a marked improvement over the existing art. It should also be noted that an exterior sample collection device (not shown) may be employed to collect the sample in the field. In that case, the collected sample can be fed into the detection system 10 as desired at a later time.

C. Second Embodiment of the Gas Flow Distribution System

Figure 3:
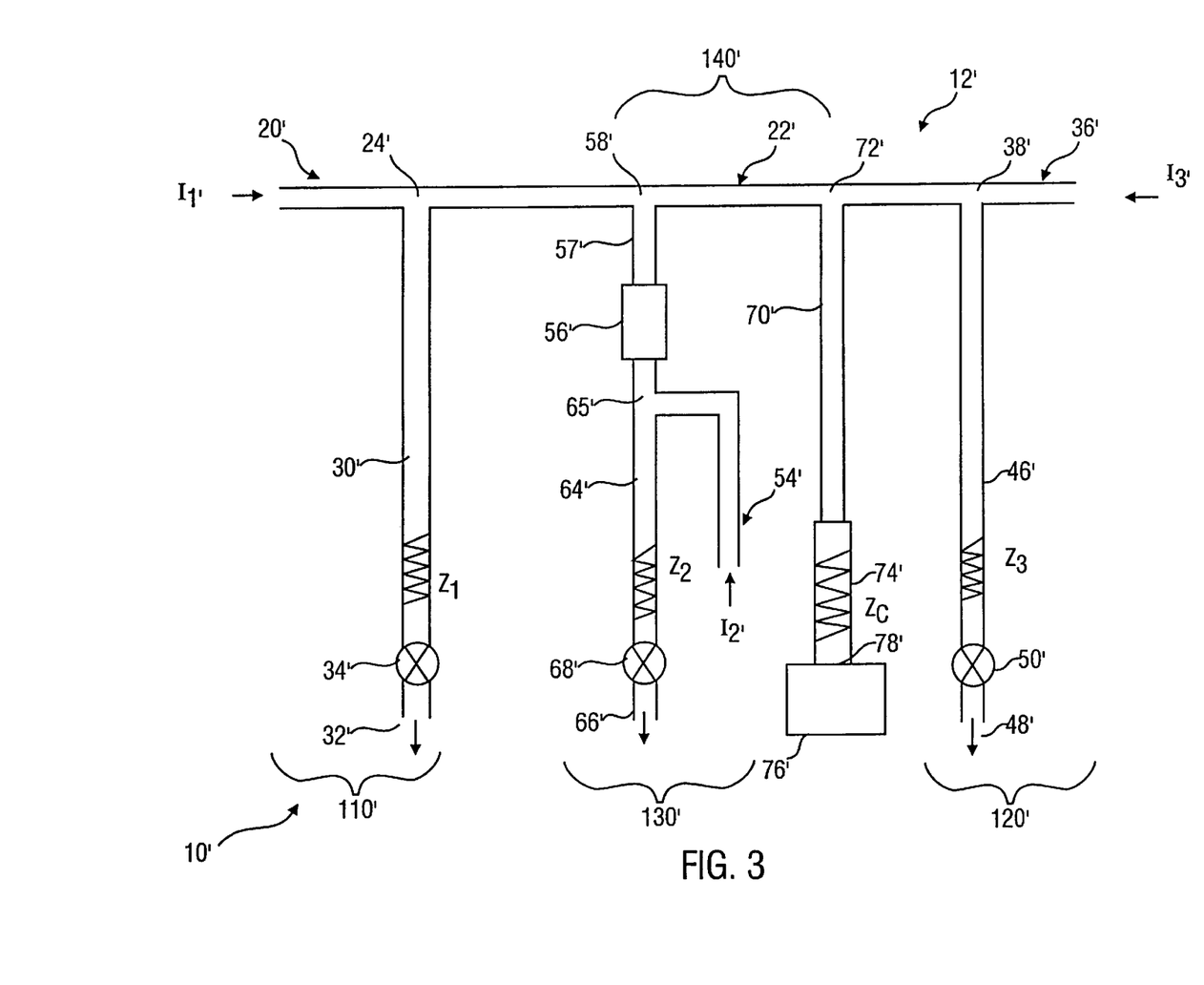
FIG. 3 is a schematic view of a second embodiment of the gas flow distribution circuit employed in the gas-chromatography mass-spectrometry trace vapor detection system.

In another embodiment of the gas flow distribution system or control circuit 12' illustrated in FIG. 3, the features of the various inlets and outlets of the system 12' are modified from those in the first system 12 of FIG. 1. Many of the components between the two systems 12, 12' are identical. For convenience, like components between the two embodiments 12, 12' are indicated by like reference numerals that are differentiated by the use of a prime in the second embodiment 12' as shown in FIG. 3.

In the flow distribution system 12', the sample bearing carrier gas inlet 20' does not include the sample flow adjustment line 26 and valve 28 of the system 12 in FIG. 1. Nor are there GC carrier gas flow adjustment line 40 and valve 42 included in the GC carrier gas inlet 36'. The distribution carrier gas flow adjustment line 60 and valve 62 of system 12 are further absent from the distribution carrier gas inlet 54' in the distribution system 12'. In this embodiment, the inlet flow rates, $I_1'$, $I_2'$, and $I_3'$ are desirably kept individually constant. The flow through the distribution system 12' and the pressure buildup therein are instead governed by the relative bore sizes of the various flow lines. A smaller bore size causes an impedance in the flow line, and restricts the flow rate through the line, which in turn increases the pressure buildup in the flow line. In contrast, the flow in the flow circuit 12 of FIG. 1 is governed not by the impedances, but by the timing of adjusting the valves 28, 34, 42, 50, 62, 68.

Accordingly, an impedance $Z_1$ in the sample bearing carrier gas diversion line 30' of a certain bore size sustains a pressure at the influent juncture 24' when the diversion valve 34' is opened during the accumulated sample delivery phase. This pressure desirably isolates the sample bearing carrier gas flow by at least substantially preventing flow of the distribution carrier gas and the GC carrier gas through the manifold 22' to the exit 32' of the sample bearing carrier gas influent circuit 110'. Similarly, during the delivery phase, an impedance $Z_3$ in the GC carrier gas diversion line 46' of a certain bore size sustains a pressure at the influent juncture 38' when the diversion valve 50' is opened. The pressure isolates the GC carrier gas flow by substantially preventing flow of the distribution carrier gas or sample bearing carrier gas through the manifold 22' to the exit 48' of the GC carrier gas influent circuit 120'. During the accumulation-detection phase, the sample bearing carrier gas flows through the accumulator 56' and the drain line 64' out the drain exit 66' while the GC carrier gas flows through the GC influent line 70' and gas chromatography column 74'. To isolate the sample bearing carrier gas from the GC carrier gas, an impedance $Z_2$ in the distribution carrier gas drain line 64' ensures appropriate pressure at the influent juncture 58', and an impedance $Z_c$ in the GC column 74' ensures sufficient pressure at the influent juncture 38'.

In sum, the impedances $Z_1$, $Z_2$, $Z_3$, and $Z_c$, together with the flow rates $I_1'$, $I_2'$, and $I_3'$, govern the pressure in the manifold 22', and are chosen to isolate the controlled flows from undesireable interfering flows throughout the entire operation cycle.

The impedances $Z_1$, $Z_2$, $Z_3$, and $Z_c$ are advantageously chosen to balance the gas flows in the flow circuit 12'. These parameters can be determined to achieve the objectives mentioned above without undue experimentation. In a preferred embodiment, $Z_3$ is chosen to be approximately equal to the column impedance $Z_c$, while the flow rate $I_2'$ is approximately equal to the flow rate $I_3'$. These parameters ensure that the flow rate to the GC column 74' is approximately equal during the delivery cycle when the distribution carrier gas moves the sample to the GC column 74' and the GC cycle when the GC carrier gas drives the sample through the GC column 74' for separation. In another embodiment, the sample bearing carrier gas flow rate $I_1'$ may be chosen to be larger than the carrier gas flow rates $I_2'$ and $I_3'$ for faster accumulation of sample from the sample bearing carrier gas in the sample accumulator 56'. In this case, $Z_1$ and $Z_2$ need also be reduced relative to $Z_3$ and $Z_c$ to prevent the sample bearing carrier gas from directly entering the GC column 74'. In addition, to prevent the sample bearing carrier gas from building up sufficient pressure in the manifold 22' to allow direct flow to the GC column 74', the ratio $Z_1/Z_c$ may be made approximately the inverse of the ratio $I_1'/I_2'$ and the ratio $Z_2/Z_c$ the inverse of the ratio $I_1'/I_3'$.

The impedances $Z_1$, $Z_2$, and $Z_3$ may be fixed or variable. A variable impedance is more difficult to achieve because the bore size of the diversion flow lines must be adjustable. Alternatively, the omitted diversion valves 34', 50', 68' may be made adjustable so as to provide adjustable flow impedances, and installed in the system 10' to accommodate the required flow sequences.

It will be understood that the above described arrangements of apparatus and the methods therefrom are merely illustrative of applications of the principles of this invention and many other embodiments and modifications may be made without departing from the spirit and scope of the invention as defined in the claims.

What is claimed is:

1. A gas flow distribution system for controlled accumulation and delivery of a sample in a diffused state for trace vapor detection and analysis, said gas flow distribution system comprising:
   a sample delivery circuit including a sample accumulator for accumulating said sample in an accumulation cycle, said sample accumulator in communication with a gas chromatography column for receiving said sample in a delivery cycle and separating said sample in a separation cycle;
   a sample bearing carrier gas influent circuit including a supply of sample bearing carrier gas to said sample delivery circuit through said sample accumulator for accumulation of said sample in said sample accumulator in real time and a sample diversion switch diverting said sample bearing carrier gas from said sample delivery circuit in said delivery cycle;
   a GC carrier gas influent circuit including a supply of GC carrier gas to said sample delivery circuit through said gas chromatography column for sample separation in real time and a GC carrier gas diversion switch diverting said GC carrier gas from said sample delivery circuit in said delivery cycle; and
   a distribution carrier gas influent circuit including a supply of distribution carrier gas to deliver said sample in said accumulator to said gas chromatography column in said delivery cycle in real time and a drain switch diverting said distribution carrier gas from said sample delivery circuit in said accumulation cycle and separation cycle.

2. The gas flow distribution system of claim 1, wherein said supply of sample bearing carrier gas, said supply of GC carrier gas, and said supply of distribution carrier gas flow at individually constant rates.

3. The gas flow distribution system of claim 1, wherein said distribution carrier gas delivers said sample to said gas chromatography column in a concentrated pulse in said delivery cycle.

4. The gas flow distribution system of claim 1, wherein said delivery cycle lasts less than about 2 seconds.

5. The gas flow distribution system of claim 1, wherein said gas chromatography column has an internal volume of less than about 1/10 c.c.

6. The gas flow distribution system of claim 1, wherein the direction of said distribution carrier gas flow through said sample accumulator in said delivery cycle is opposite from the direction of said sample bearing carrier gas flow through said sample accumulator in said accumulation cycle.

7. The gas flow distribution system of claim 1, wherein said sample diversion switch, GC carrier gas diversion switch, and distribution carrier gas diversion switch have small internal volume and are operable at high temperature.

8. The gas flow distribution system of claim 1, wherein the distance said sample in said sample accumulator travels to reach said gas chromatography column in said delivery cycle is less than about 5 cm.

9. The gas flow distribution system of claim 1, wherein said GC carrier gas diversion switch and said sample bearing carrier gas diversion switch are both closed to prevent flow of respective GC carrier gas and sample bearing carrier gas out from respective circuits and said drain switch is open to enable flow of said distribution carrier gas out from said distribution carrier gas influent circuit whereby said accumulation cycle and said separation cycle occur substantially simultaneously.

10. The gas flow distribution system of claim 1, wherein said accumulator comprises a cold trap for accumulating said sample in said accumulation cycle, said cold trap being electrically heated by a current pulse to deliver said sample to said GC column in said delivery cycle.

11. The gas flow distribution system of claim 1, wherein said sample bearing carrier gas influent circuit further comprises a sample bearing carrier gas adjustment line with a sample bearing carrier gas adjustment valve downstream of said adjustment line.

12. The gas flow distribution system of claim 1, wherein said GC carrier gas influent circuit further comprises a GC carrier gas adjustment line with a GC carrier gas adjustment valve downstream of said adjustment line.

13. The gas flow distribution system of claim 1, wherein said distribution carrier gas influent circuit further comprises a distribution carrier gas adjustment line with a distribution carrier gas adjustment valve downstream of said adjustment line.

14. The gas flow distribution system of claim 1, wherein said sample diversion switch diverts said sample bearing carrier gas in said delivery cycle through a sample diversion line, said GC carrier gas diversion switch diverts said GC carrier gas in said delivery cycle through a GC carrier gas diversion line, and said distribution carrier gas diversion switch diverts said distribution carrier gas in said accumulation cycle and said separation cycle through a distribution carrier gas diversion line.

15. The gas flow distribution system of claim 14, wherein said sample diversion line has a sample carrier gas bore diameter that impedes flow therethrough, said GC carrier gas diversion line has a GC carrier gas bore diameter that impedes flow therethrough, and said distribution carrier gas diversion line has a distribution carrier gas bore diameter that impedes flow therethrough, said bore diameters being selected to balance gas flow in said gas flow distribution system during said accumulation cycle, delivery cycle, and separation cycle.

16. The gas flow distribution system of claim 1, wherein said sample bearing carrier gas influent circuit and said GC carrier gas influent circuit separately communicate with said sample delivery circuit through respective communication means thereby defining a sample delivery path and said sample diversion switch and GC diversion switch are each disposed in parallel arrangement with said sample delivery path.

17. In a trace vapor detection system, a gas control circuit for supplying a sample to a gas chromatography column, comprising:
   a supply of sample bearing carrier gas including a sample;
   a supply of carrier gas;
   a sample accumulating means;
   a means for directing said sample bearing carrier gas to said sample accumulating means for accumulation of said sample in said sample accumulating means in real time and for diverting said carrier gas from entering said sample accumulating means in an accumulation mode;
   a means for transferring said sample accumulated in said sample accumulating means to said gas chromatography column for separation in real time with said carrier gas and for diverting said sample bearing carrier gas from entering said sample accumulating means and said gas chromatography column in a delivery mode; and
   a circuit in common communication with said sample accumulating means, said means for directing, said means for transferring and said gas chromatography column.

18. The gas control circuit of claim 17, wherein said sample accumulating means comprises a cold trap with wiring connected to an electrical source.

19. The gas control circuit of claim 17, further comprising a means for driving said sample delivered to said gas chromatography column in said delivery mode through said gas chromatography column toward a mass spectrometer in real time and diverting said sample and sample bearing carrier gas from entering said gas chromatography column in a detection mode, said means including a GC carrier gas line connecting said supply of carrier gas to said gas chromatography column, a sample transfer diversion line connected to said sample accumulating means, and a sample bearing carrier gas diversion line connected to said supply of sample bearing carrier gas.

20. A gas flow circuit for real-time accumulation and delivery of a sample to a gas chromatography column, said gas flow circuit comprising:
   a manifold;
   a sample influent line for introducing a sample bearing carrier gas into said manifold, said sample influent line including a sample diversion line with a sample diversion valve;
   a detection carrier gas influent line for introducing a detection carrier gas into said manifold, said detection carrier gas influent line being in communication with said gas chromatography column through said manifold and including a detection carrier gas diversion line with a detection carrier gas diversion valve;
   a distribution carrier gas influent line for introducing a distribution carrier gas into said manifold, said distribution carrier gas influent line including a distribution carrier gas diversion line with a distribution carrier gas diversion valve;
   an accumulator disposed between said distribution carrier gas influent line and said manifold, said accumulator being downstream of said sample influent line and manifold and upstream of said distribution carrier gas diversion line, and said gas chromatography column being downstream of said detection carrier gas influent line and manifold, when said distribution carrier gas diversion valve is opened and said sample diversion valve and detection carrier gas diversion valve are closed, and said accumulator being downstream of said distribution carrier gas influent line and upstream of said manifold and gas chromatography column when said distribution carrier gas diversion valve is closed and said sample diversion valve and detection carrier gas diversion valve are opened.

21. The gas flow circuit of claim 20, wherein said manifold, accumulator, and gas chromatography column are placed inside an oven at a temperature of more than about 200° C., and said sample diversion valve, detection carrier gas diversion valve, and distribution carrier gas diversion valve are disposed exterior of said oven.

* * * * *